United States Patent
Baker

[11] Patent Number: 5,865,848
[45] Date of Patent: Feb. 2, 1999

[54] DYNAMIC INTERVERTEBRAL SPACER AND METHOD OF USE

[75] Inventor: Gregg S. Baker, Geneva, Fla.

[73] Assignees: Artifex, Ltd.; BHC Engineering, L.P., both of Maitland, Fla.

[21] Appl. No.: 928,728

[22] Filed: Sep. 12, 1997

[51] Int. Cl.$^6$ ............................................. A61F 2/44
[52] U.S. Cl. ............................................. 623/17; 606/61
[58] Field of Search ................................ 623/17; 606/61

[56] References Cited

U.S. PATENT DOCUMENTS

| | | | |
|---|---|---|---|
| 4,401,112 | 8/1983 | Rezaian | 128/92 B |
| 4,501,269 | 2/1985 | Bagby | 128/92 G |
| 4,553,273 | 11/1985 | Wu | 623/18 |
| 4,554,914 | 11/1985 | Kapp et al. | 128/92 C |
| 4,863,476 | 9/1989 | Shepperd | 623/17 |
| 4,936,848 | 6/1990 | Bagby | 623/17 |
| 4,961,740 | 10/1990 | Ray et al. | 606/61 |
| 5,015,255 | 5/1991 | Kuslich | 623/17 |
| 5,026,373 | 6/1991 | Ray et al. | 606/61 |
| 5,055,104 | 10/1991 | Ray | 606/61 |
| 5,059,193 | 10/1991 | Kuslich | 606/61 |
| 5,062,845 | 11/1991 | Kuslich et al. | 606/80 |
| 5,127,912 | 7/1992 | Ray et al. | 606/61 |
| 5,263,953 | 11/1993 | Bagby | 606/61 |
| 5,300,073 | 4/1994 | Ray et al. | 606/61 |
| 5,364,399 | 11/1994 | Lowery et al. | 606/69 |
| 5,390,683 | 2/1995 | Pisharodi | 623/17 |
| 5,425,772 | 6/1995 | Brantigan | 623/17 |
| 5,445,639 | 8/1995 | Kuslich et al. | 606/80 |
| 5,458,638 | 10/1995 | Kuslich et al. | 623/17 |
| 5,458,641 | 10/1995 | Jimenee | 606/61 |
| 5,470,333 | 11/1995 | Ray | 606/61 |
| 5,489,307 | 2/1996 | Kuslich et al. | 623/17 |
| 5,489,308 | 2/1996 | Kuslich et al. | 623/17 |
| 5,514,180 | 5/1996 | Heggeness et al. | 623/17 |
| 5,522,899 | 6/1996 | Michelson | 623/17 |
| 5,527,312 | 6/1996 | Ray | 606/61 |
| 5,531,745 | 7/1996 | Ray | 606/61 |
| 5,531,747 | 7/1996 | Ray | 606/61 |
| 5,549,679 | 8/1996 | Kuslich | 623/17 |
| 5,554,191 | 9/1996 | Lahille | 623/17 |
| 5,571,189 | 11/1996 | Kusich | 623/17 |
| 5,591,235 | 1/1997 | Kuslich | 623/17 |
| 5,609,635 | 3/1997 | Michelson | 606/61 |
| 5,653,763 | 8/1997 | Errico | 623/17 |

*Primary Examiner*—Michael J. Milano
*Attorney, Agent, or Firm*—Finnegan, Henderson, Farabow, Garrett, & Dunner, L.L.P.

[57] ABSTRACT

A spinal fusion implant assembly for spacing vertebrae and method of using the implant are provided. The implant includes two components each having a vertebral contact surface, a pair of side portions, and an end plate. The two components are complementary such that when placed together they form a whole. Each of the sides has a high point and a low point, such that a sloped edge of each side is defined between the high point and the low point, and the slope of the first sides is complementary to the slope of the second sides. The device also includes a translation mechanism for providing relative motion between the components.

36 Claims, 8 Drawing Sheets

DYNAMIC INTERVERTEBRAL SPACER AND METHOD OF USE

BACKGROUND OF THE INVENTION

1. Field of the Invention

The present invention relates to a dynamic intervertebral spacer implant to be placed into an intervertebral space left after the removal of damaged spinal disc material.

2. Description of the Related Art

Historically, methods of fusing two adjacent vertebrae of the spine intervertebrally have used implants of either natural bone or a synthetic material and having fixed dimensions. Although the devices are available in a range of sizes, the devices are not adjustable by the surgeon during the surgical procedure. Therefore, the surgeon must choose the size which most closely matches the desired height, length and width dimensions, and then make the device fit. This procedure may entail further resection of the bone, or addition of natural bone, attained from either an inventoried bone bank or a patient donor site. The procedure results in relatively long and more invasive surgeries which present a danger to the patient.

In cases where an all bone implant is used, the bone is shaped to complement the surgeon-prepared cavity into which it is to be implanted. When a synthetic implant is used, the bone is pulverized and packed into the interstices of the device, in order to promote bony ingrowth. Over time, fusion is accomplished by the growth of natural bone in the neighboring, subject vertebrae into the implant.

Improvements in design and materials have resulted in stronger implants. However, due to the usual shapes used for fusion implants, they are still subject to fracture.

SUMMARY OF THE INVENTION

The present invention is directed to a spinal fusion implant that obviates the limitations and disadvantages of prior implants.

Additional features and advantages of the present invention will be set forth in the description which follows, and in part will be apparent from the description, or may be learned by practice of the invention. The objectives and advantages of the invention will be realized and attained by means of the elements and combinations particularly pointed out in the appended claims.

To achieve these and other advantages and in accordance with one aspect of the present invention, as embodied and broadly described herein, a spinal fusion implant is provided in the form of a fusion implant assembly having first and second complementary portions, each portion having a vertebral contact surface, two sides and an end plate. The complementary portions fit together to form a whole implant. A translation mechanism is provided to obtain relative motion between the complementary portions.

According to another aspect of the invention, a spinal fusion implant assembly for spacing vertebrae is provided, that includes a first component having a first vertebral contact surface, a pair of side portions extending upwards from the first surface, and a first end plate portion extending upwards from the first surface. A second component having a second vertebral contact surface, a pair of side portions extending downwards from the second surface, and a second end plate portion extending downwards from the second surface, each of the side portions having a high point and a low point, such that a sloped edge of each side portion is defined between the high point and the low point, and wherein the slope of the first side portions is complementary to the slope of the second side portions, and a translation mechanism for providing relative motion between the components.

According to yet another embodiment of the present invention, a spinal fusion implant kit is provided, the kit comprising at least two spinal fusion implant devices, wherein each implant device comprises first and second complementary portions, each portion having a vertebral contact surface, two sides and an end plate, said portions fitting together to form a whole, and a translation mechanism for providing relative motion between the complementary portions, wherein the at least two spinal fusion implant devices are of different sizes.

According to another embodiment of the present invention, a method of implanting a fusion assembly between adjacent vertebrae is provided, the method comprising the steps of gaining exposure to the surgical site, removing disc material from between adjacent vertebrae, preparing the end plates of the adjacent vertebrae to receive the implant, creating a cavity of desired dimensions for the implant, placing the implant within the cavity, providing relative movement between components of the implant until the implant reaches desired dimensions, and closing the surgical site.

According to a further embodiment of the present invention, a method of correcting spondylolisthesis is provided, the method including the steps of gaining access to the surgical site, selecting a fusion implant assembly including complementary components, locating the implant assembly between a normal vertebrae and a slipped vertebrae, providing relative motion between the complementary components of the fusion implant assembly to adjust the height between the two vertebrae and to move the slipped vertebrae into a more normal position, and closing the surgical site.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

The present invention relates to an implant and method of use for spinal fusion. Generally, an implant is used to replace portions of damaged disc material between adjacent vertebrae to stabilize the spine and to eliminate motion at that location.

Figure 1A:
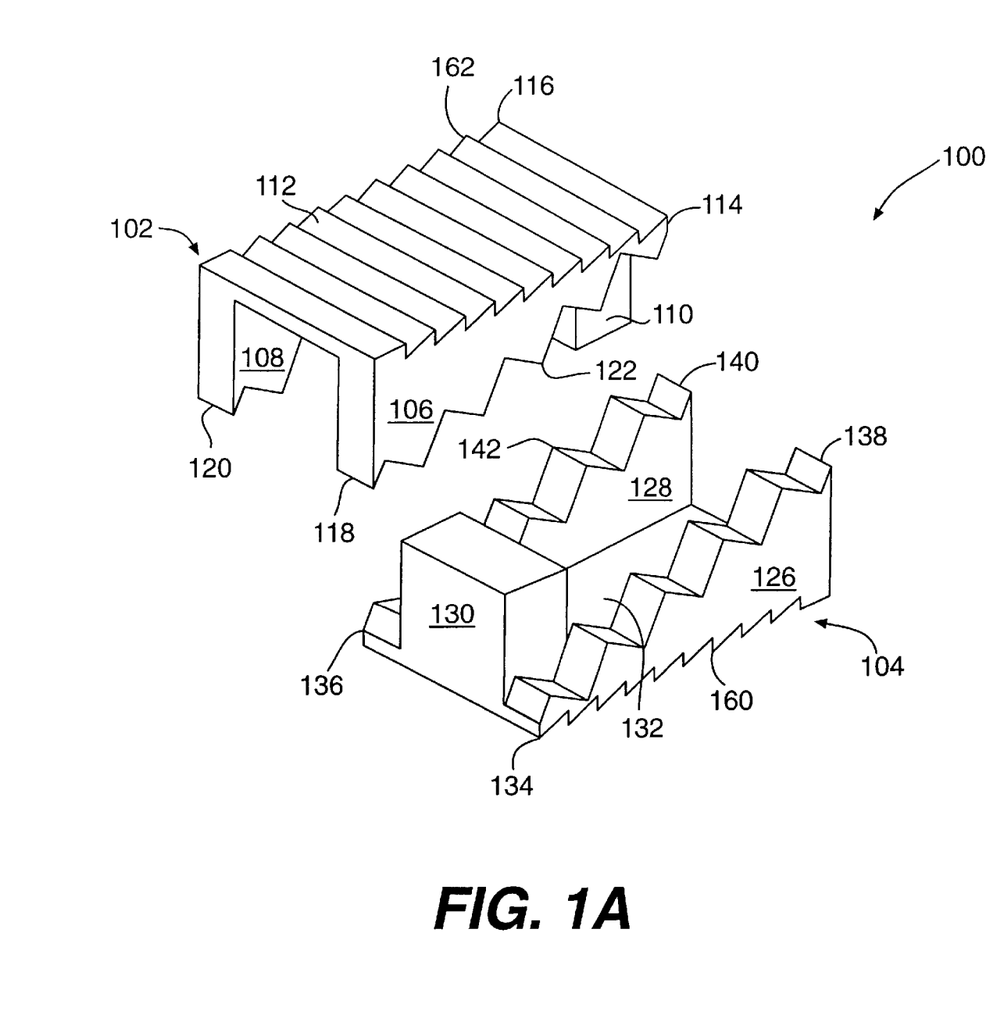
FIGS. 1A and 1B are isometric views of an embodiment of the spinal implant assembly of the present invention showing the two separate components of the assembly.
Figure 1B:
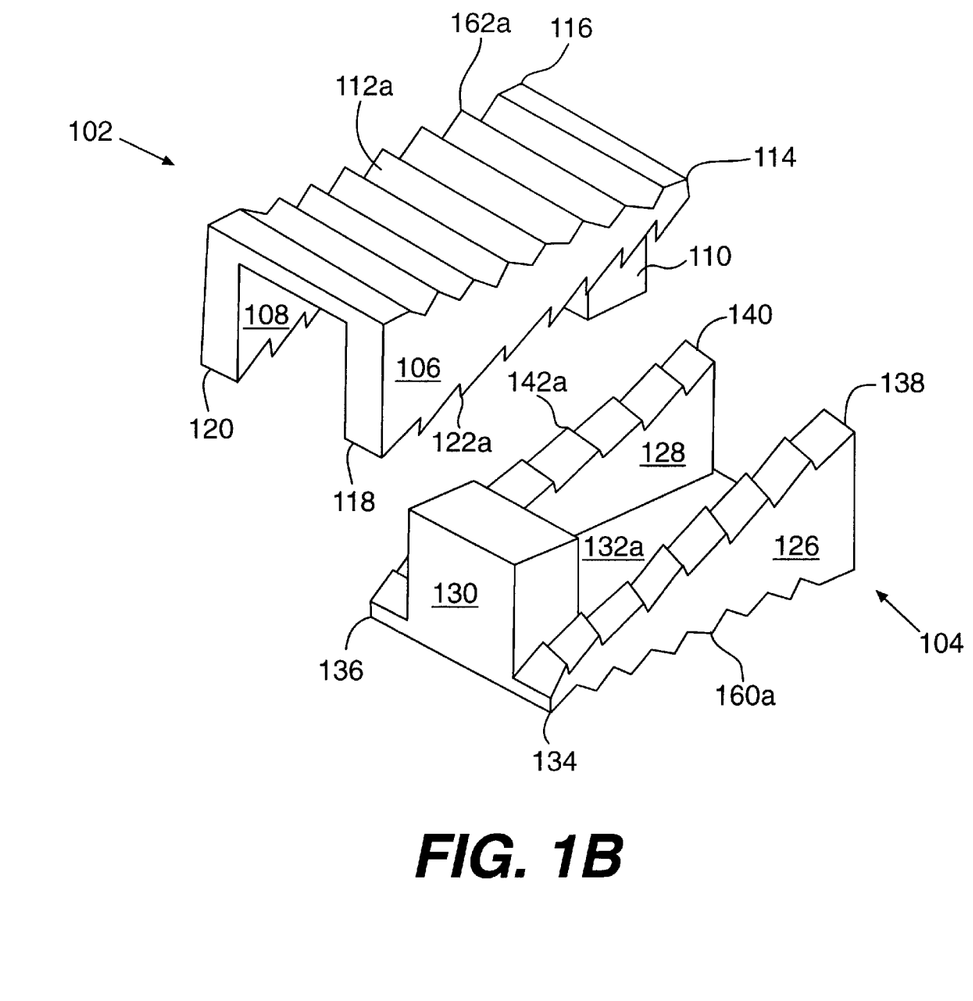
Figure 2:
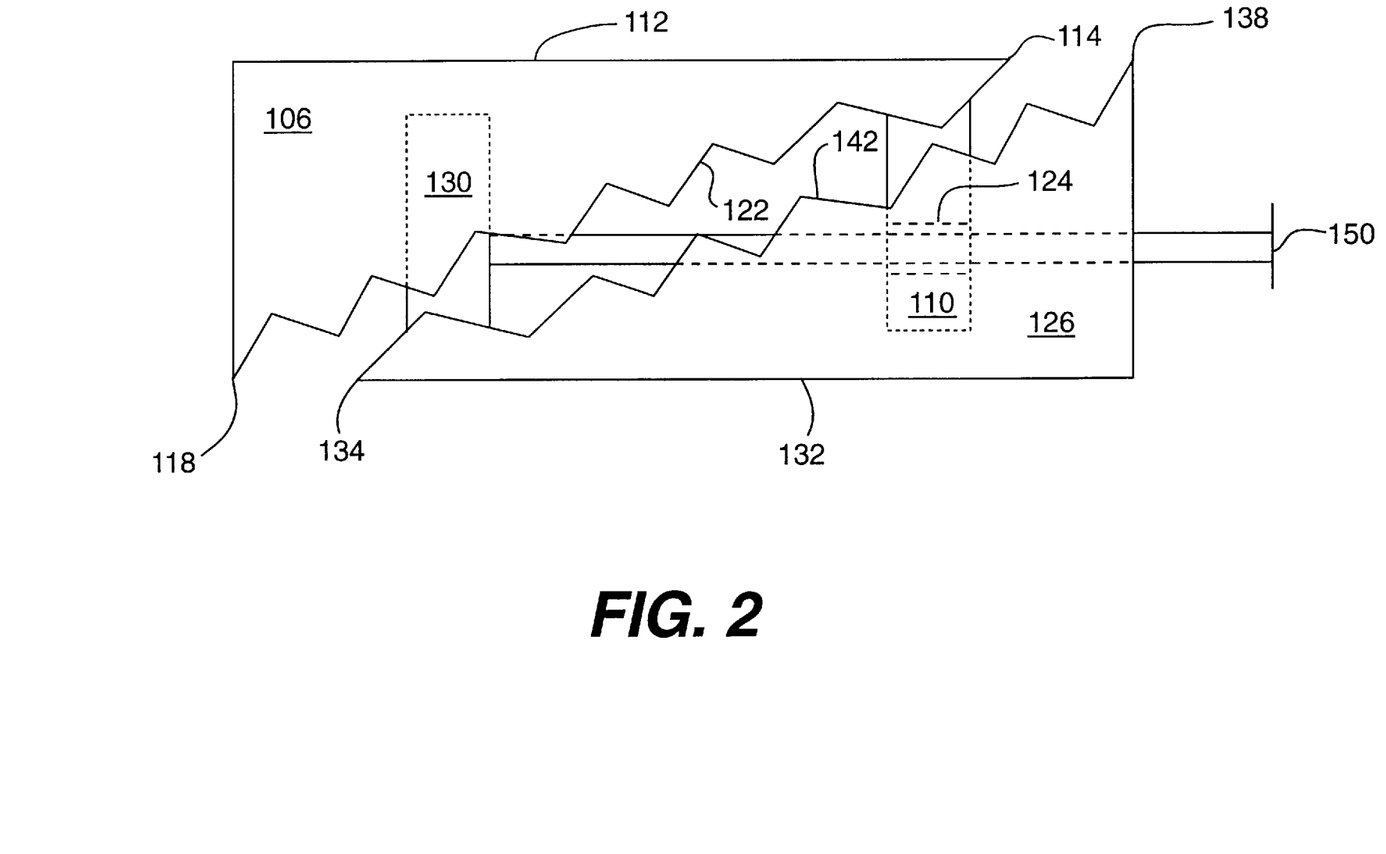
FIGS. 2–4 are side views of the components of the assembly of FIG. 1A as they are moved relative to one another.

The present invention, as embodied in herein and shown in FIGS. 1A and 1B, is a spinal fusion implant 100 having a top component 102 and a bottom component 104, each component 102, 104, forming a ramp and making up half of the device 100. Top component 102 includes a pair of side portions 106, 108, an end plate 110, and a vertebral contact surface 112, 112a for contacting and gripping the vertebrae when implanted. Vertebral contact surface 112, 112a may have a rough surface including protrusions or teeth 160, 160a to promote gripping of the vertebral end plate. In the end plate 110, there is a tapped, threaded hole 124 for receiving a translation mechanism to provide relative motion between top component 102 and bottom component 104. As can be seen in FIG. 2, each side portion 106, 108, of the top component 102 has a low point 118, 120, where the height of the side wall is greatest, and a high point 114, 116, where the height of the wall is lowest. Defined between these low points 118, 120 and these high points 114, 116, is the slope of the side portions, or the ramp. Along the slope of each side portion 106, 108, the top component 102 may include a plurality of complementary wedging ramps in the form of ridges or steps 122, 122a.

Referring again to FIGS. 1A, 1B, and 2, it can be seen that the bottom component 104 is the complement to top component 102 and together they form a whole. Bottom component 104 includes a pair of side portions 126, 128, an endplate 130, and a vertebral contact surface 132, 132a for contacting and gripping the vertebrae when implanted. Vertebral contact surface 132, 132a may have a rough surface including protrusions or teeth 160, 160a to promote gripping of the vertebral end plate. As can be seen in FIG. 2, each side portion 126, 128, of the bottom component 104 has a high point 138, 140, where the height of the side wall is greatest, and a low point 134, 136, where the height of the wall is lowest. Defined between these high points 138, 140 and these low points 134, 136, is the slope of the side portions or the ramp. Along the slope of each side portion 126, 128, the bottom component 104 may include a plurality of complementary wedging ramps in the form of ridges or steps 142, 142a. The particular shape of the texture 160, 160a, 162, 162a of vertebral contacting surfaces 112, 112a, 132, and 132a may vary, as may the angles used to form the complementary wedging ramps 122, 122a, 142, and 142a. FIGS. 1A and 1B show two different variations of these surfaces, FIG. 1B is presently the preferred embodiment.

Figure 3:
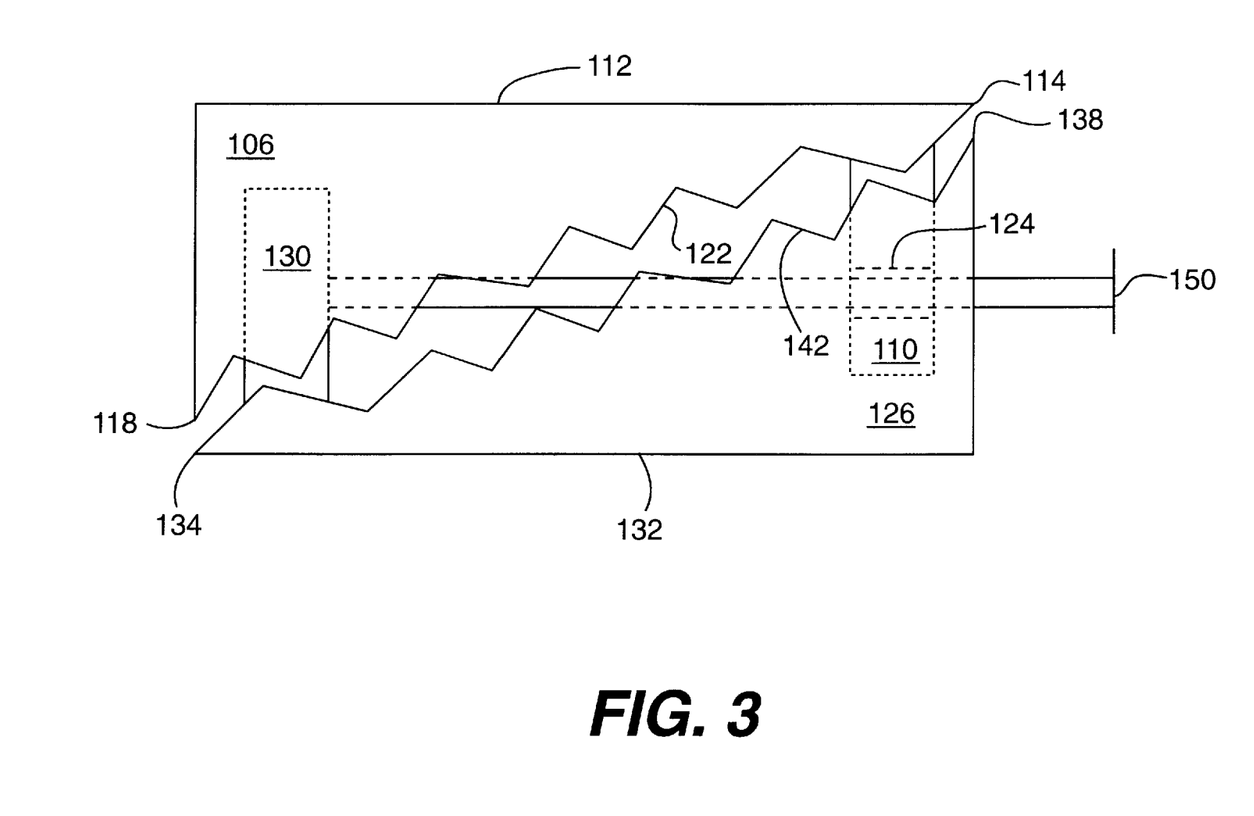
Figure 4:
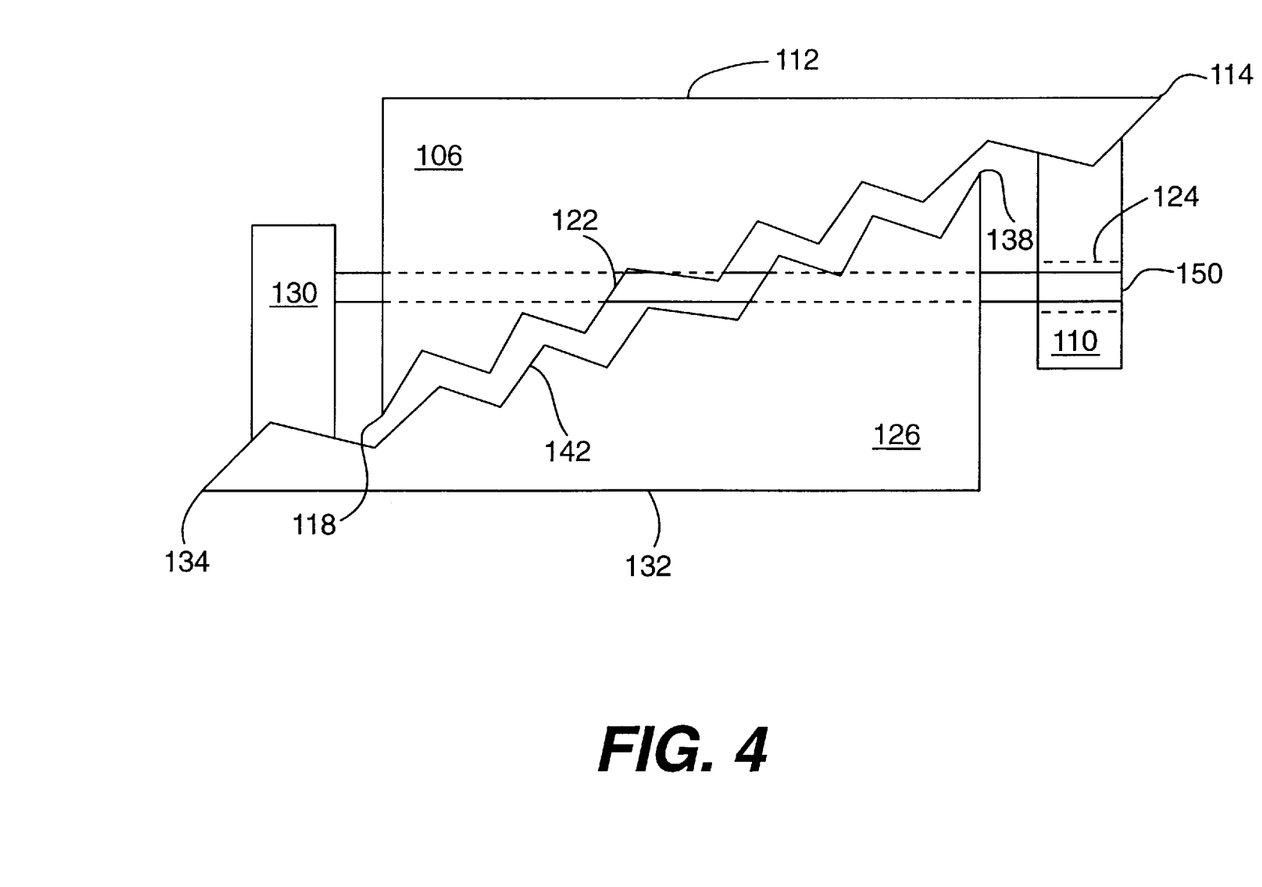

As can be seen in FIGS. 2–4, the slope of side portions 106, 108 is complementary to the slope of side portions 126, 128 such that the top component 102 and bottom component 104 fit together to form a whole 100. In order to provide relative motion between the top component 102 and the bottom component 104, a translation mechanism is used. In the preferred embodiment an installation bolt 150 is used. Bolt 150 passes through hole 124 until its end abuts the inner surface of the end plate 130 of the bottom component. By tightening bolt 150, the length of the bolt within the implant increases, pushing against the inner surface of end plate 130. As the pressure increases from bolt 150, relative motion between the top and bottom components is provided, the ridges or steps 122, 122a, 142, and 142a allowing the top and bottom pieces to move in a ratcheting manner, preventing slippage of the components to their original positions.

As shown in FIGS. 2–4, as bolt 150 is tightened it pushes against end plate 130, causing end plate 130 to move away from endplate 110. As the distance between end plates 110 and 130, increases, top component 102 moves upwardly along the slope of the bottom component, resulting in a change in the height of implant assembly 100.

Alternatively, it is possible to start with implant 100 in an offset position which allows a lower initial height of the device and also provides greater potential for relative motion between the components. As shown in FIG. 2, top component is shifted to the left, resulting in a lower height of the implant. This particular starting configuration is useful when the surgeon's goal is to align the adjacent vertebrae by forcing relative movement of the vertebrae through the vertebrae contact surfaces of the implant. As above, an installation bolt 150 is used. Bolt 150 passes through hole 124 until its end abuts the inner surface of the end plate 130 of the bottom component. By tightening bolt 150, the length of the bolt within the implant increases, pushing against the inner surface of end plate 130. As the pressure increases from bolt 150, relative motion between the top and bottom components is provided, the ridges or steps 122, 142 allowing the top and bottom pieces to move in a ratcheting manner, preventing slippage of the components to their original positions. As shown in FIGS. 2–4, as bolt 150 is tightened it pushes against end plate 130, causing endplate 130 to move away from endplate 110. As the distance between end plates 110 and 130, increases, top component 102 moves upwardly along the slope of the bottom component, resulting in a change in the height of implant assembly 100.

Top and bottom components 102, 104 may be made from any material of suitable strength and rigidity, and it is preferred that a biocompatible material be used. Examples of appropriate materials are titanium and stainless steel. In addition, the surfaces of the spinal fusion implant 100 may be coated in order to promote bony ingrowth. Desirable coatings for promoting bony ingrowth may include a porous coating such as a plasma spray, sintered beads, or other porous coatings such as hydroxyapatite.

Figure 5:
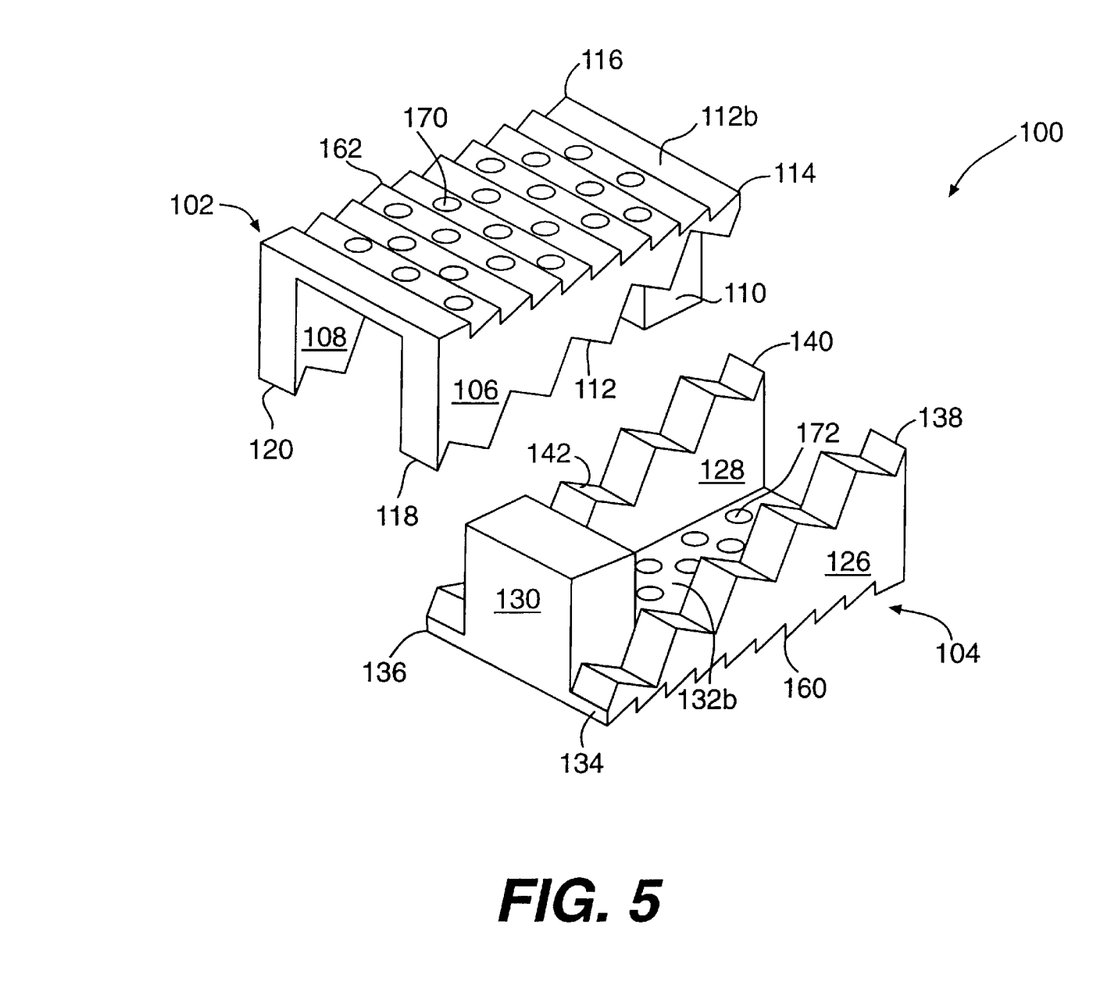
FIG. 5 is a side view of a second embodiment of the spinal implant assembly of the present invention.

In an alternative embodiment, as shown in FIG. 5, the vertebral contact surfaces 112b, 132b, may contain perforations 170, 172. The perforations will allow better bone growth, particularly macro-growth of the bone. In a non-preferred example, it would be possible, although unnecessary, for the surgeon to pack the implant with bone material and allow the bone material to promote bony growth. In such an instance, the device should be packed before implantation, then rotation of the installation bolt to move the device components to their desired positions would also perform the function of pressing or squeezing the bony material out of the perforations between the vertebral contact surface and the vertebral end plates.

Figures 6A, 6B:
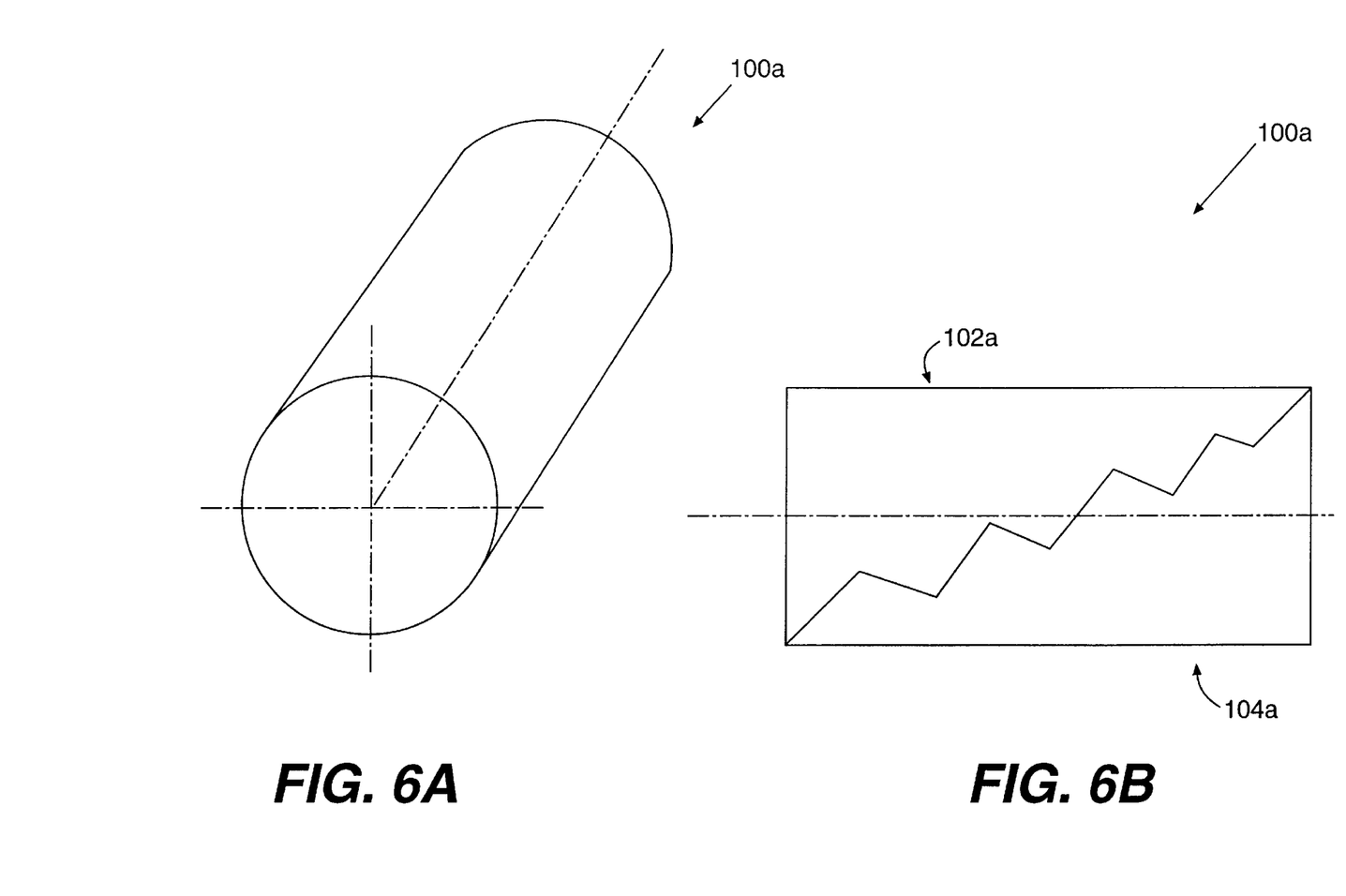
FIGS. 6A and 6B are side views of a third embodiment of the spinal implant assembly of the present invention showing the shape of the components.

As seen in FIGS. 1–5, the spinal fusion implant 100 has a generally rectangular shape. Due to the rectangular shape of the contact surfaces, the implant has mechanical performance which is superior to other devices, reacting better to compressive forces applied in vivo. However, it is possible, as shown in FIGS. 6A and 6B, to use a device 100a with a circular cross-section that is cylindrical in shape. A device with a circular cross section includes top component 102a and bottom component 104a and is easier to install in the cavity within the spine. It is contemplated that devices of other shapes may be used.

Figure 7:
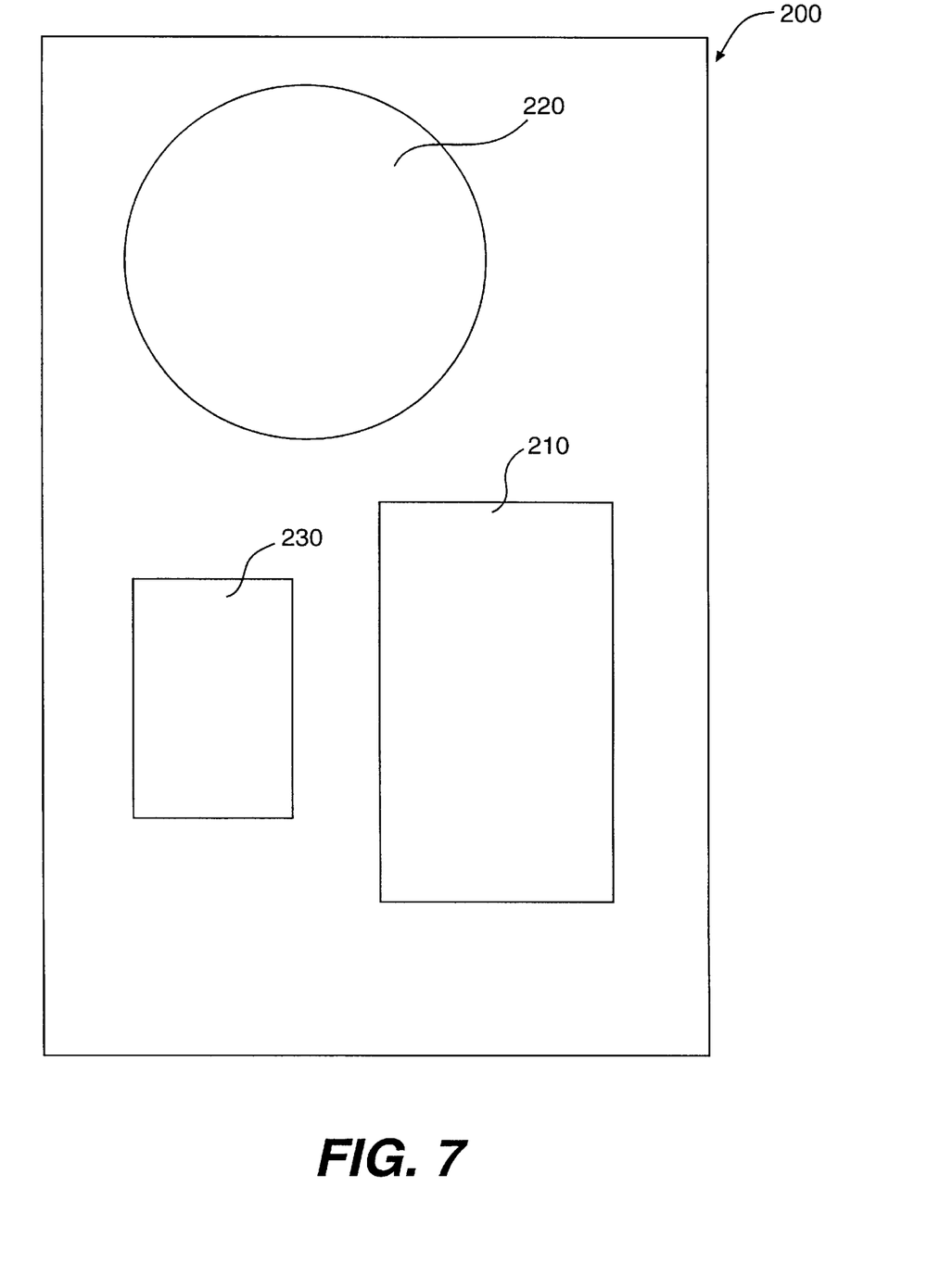
FIG. 7 is a cross section of an embodiment of a kit comprising the spinal implant assemblies of the present invention.

Spinal fusion implant 100 may be used in any area of the spine, and therefore, encompasses a wide range of sizes. Referring, for example, to the rectangular embodiment of the invention, the device might have a length L between 8 and 30 mm, a width W between 5 and 20 mm and a height H between 5 and 25 mm. As embodied in FIGS. 1–6B, the device uses two components, each having the same length, width and height. However, it is possible, should a surgeon seek to use a size not provided within a kit of different size implants, to mix different size components to achieve a desired size. For example, if the implant came in heights of 10 mm, 12 mm, 14 mm, and 16 mm, and the surgeon wished for an implant with a height of 15 mm, it would be possible for the surgeon to use a component from the 14 mm device and a component from the 16 mm device to devise a 15 mm device. Thus, because a surgeon cannot be certain he has the correct size device until the cavity is created within the spine, it is desirable to provide the surgeon with a kit 200 of different size and shaped devices 210, 220, 230, as shown in FIG. 7, which may be used as provided or the components may be mixed to provide custom size devices. Alternatively, components having different slopes may be used together to achieve a device with different angles or ramps of different slopes, such that the top and bottom planes of the device would not be parallel.

In use, the surgeon must first prepare the surgical site and gain exposure to the interspace to be operated on. The surgeon may use either an anterior or posterior approach. Once the surgical site is accessed, some or all damaged disc material between the two vertebrae is removed. Now that the surgeon has prepared the area, he must create the cavity for the device. The surgeon determines the size of the cavity to be created based on the size of the area available. Because there is a wide range of implant sizes available and because each implant is adjustable, he need not remove excess bone or prolong the surgery to fit the cavity to a single sized implant. After the cavity is complete, the surgeon chooses a spinal fusion implant of a desired size from a kit of different size spinal fusion implants. Although an unnecessary step, if the implant has perforations, the surgeon may choose to pack the implant with bone material. After the implant is selected and prepared, it is inserted into the cavity prepared by the surgeon. Next, the surgeon tightens the bolt within the device such that there is relative movement between the two components of the device to adjust the height and/or position of the device. This continues until the device fits snugly within the cavity and the surgeon feels that the device is properly situated.

In an alternative method, the implant may be used to correct spondylolisthesis, a condition where the vertebrae has slipped out of alignment resulting in a loss in disc height. The procedure is substantially the same as outlined above, with the exception that the components of the device are moved, by turning of the installation bolt, to bring the vertebrae back into alignment, with the device placed between them, such that the device corrects for some or all loss in disc height.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A spinal fusion implant assembly for stabilizing vertebrae comprising:

a first component having a first vertebral contact surface, a pair of side portions extending upwards from said first surface, and a first end plate portion extending upwards from said first surface;

a second component having a second vertebral contact surface, a pair of side portions extending downwards from said second surface, and a second end plate portion extending downwards from said second surface;

each of said side portions having a high point and a low point on respective ends of the side portion, such that a sloped edge of each side portion is defined between the high point and the low point, and wherein the slope of the first side portions is complementary to the slope of the second side portions; and a translation mechanism for providing relative movement between the first and second components in a horizontal direction.

2. The assembly of claim 1, wherein the assembly, when assembled, has a rectangular cross section.

3. The assembly of claim 1, wherein the assembly, when assembled, has a rounded cross section.

4. The assembly of claim 1, wherein the first and second contact surfaces are perforated.

5. The assembly of claim 1, wherein one of the end plates includes a threaded hole for a bolt.

6. The assembly of claim 5, wherein the translation mechanism is an installation bolt.

7. The assembly of claim 1, wherein the assembly comprises a biocompatible material.

8. The assembly of claim 1, wherein the first and second components have a coating for promoting bony ingrowth.

9. The assembly of claim 1, wherein the first and second vertebral contact surfaces have textured areas for grasping the vertebrae.

10. The assembly of claim 9, wherein the textured areas are ridges.

11. The assembly of claim 1, wherein the sloped edges of each of said first and second side portions have complementary steps, such that the first side portions fit to the second side portions.

12. The assembly of claim 1, wherein the translation mechanism also provides relative movement between the first and second components in a vertical direction.

13. A spinal fusion implant assembly for stabilizing vertebrae comprising:

a first component having a first vertebral contact surface, a pair of side portions extending upwards from said first surface, and a first end plate portion extending upwards from said first surface;

a second component having a second vertebral contact surface, a pair of side portions extending downwards from said second surface, and a second end plate portion extending downwards from said second surface;

each of said side portions having a high point and a low point, such that a sloped edge of each side portion is defined between the high point and the low point, wherein the slope of the first side portions is complementary to the slope of the second side portions, and wherein a greatest height of each side portion for each pair of side portions is located at one end of the component and the end plate of each component is located at an opposite end of the component; and a translation mechanism for providing relative motion between the components.

14. A spinal fusion implant assembly for stabilizing vertebrae comprising:

a first component having a first vertebral contact surface, a pair of side portions extending upwards from said first surface, and a first end plate portion extending upwards from said first surface;

a second component having a second vertebral contact surface, a pair of side portions extending downwards from said second surface, and a second end plate portion extending downwards from said second surface;

each of said side portions having a high point and a low point, such that a sloped edge of each side portion is defined between the high point and the low point, the sloped edges of each of said first and second side portions having complementary slopes and complementary ridges, such that the first side portions fit to the second side portions; and a translation mechanism for providing relative motion between the components.

15. A fusion implant assembly comprising:

first and second complementary portions, each portion having a vertebral contact surface, two sides and an end plate, said portions fitting together to form a whole, wherein the vertebral contact surface of the first portion is positioned above the vertebral contact surface of the second portion; and means for providing relative movement between the first and second complementary portions in a horizontal direction.

16. The fusion implant assembly of claim 15, wherein each of said sides includes a high point and a low point, such that a sloped edge of each side is defined between the high point and the low point, and wherein the slope of the first sides is complementary to the slope of the second sides.

17. The fusion implant assembly of claim 15, wherein the assembly, when assembled, has a rectangular cross section.

18. The fusion implant assembly of claim 15, wherein the assembly, when assembled, has a rounded cross section.

19. The fusion implant assembly of claim 15, wherein the first and second vertebral contact surfaces are perforated.

20. The fusion implant assembly of claim 15, wherein one of the end plates includes a threaded hole for a bolt.

21. The fusion implant assembly of claim 20, wherein the translation mechanism is an installation bolt.

22. The fusion implant assembly of claim 15, wherein the translation mechanism also provides relative movement between the first and second components in a vertical direction.

23. A fusion implant assembly comprising:

first and second complementary portions, each portion having a vertebral contact surface, two sides and an end plate, said portions fitting together to form a whole, each of said sides including a high point and a low point, such that a sloped edge of each side is defined between the high point and the low point, the slope of the first sides being complementary to the slope of the second sides, and wherein a greatest height of each side for each pair of sides is located at one end of the component and the end plate of each component is located at an opposite end of the component; and a translation mechanism for providing relative motion between the complementary portions.

24. A fusion implant assembly comprising:

first and second complementary portions, each portion having a vertebral contact surface, two sides and an end plate, said portions fitting together to form a whole, each of said sides including a high point and a low point, such that a sloped edge of each side is defined between the high point and the low point, wherein the slope of the first sides is different from the slope of the second sides; and a translation mechanism for providing relative motion between the complementary portions.

25. A method of implanting a fusion assembly between adjacent vertebrae comprising:

gaining exposure to the surgical site;

removing disc material from between adjacent vertebrae;

creating a cavity of desired dimensions for the fusion assembly;

placing the fusion assembly with the cavity;

providing relative horizontal movement between vertebral contact surfaces of components of the fusion assembly to adjust the size or shape of the fusion assembly; and closing the surgical site.

26. The method of claim 25 wherein the providing of relative movement includes tightening a screw mechanism.

27. The method of claim 25 wherein the method further includes removing a translation mechanism before closing the surgical site.

28. The method of claim 25 wherein gaining exposure to the surgical site is done in either an anterior or posterior approach.

29. The method of claim 25 wherein the method further includes:

packing the fusion assembly, if it contains perforations, with a bone material prior to inserting the fusion assembly into the cavity; and displacing the bone material through the perforations by actuating a translation mechanism.

30. A method of correcting spondylolisthesis, including:

gaining access to the surgical site;

selecting a fusion implant assembly including complementary components;

locating the implant assembly between a normal vertebrae and a slipped vertebrae;

providing relative horizontal and vertical movement between vertebral contact surfaces of the complementary components of the fusion implant assembly to adjust the height between the two vertebrae and to move the slipped vertebrae into its normal position; and closing the surgical site.

31. A spinal fusion implant kit comprising:

at least two spinal fusion implant devices, wherein each implant device comprises:

first and second complementary portions, each portion having a vertebral contact surface, two sides and an end plate, said portions fitting together to form a whole, wherein the vertebral contact surface of the first portion is positioned above the vertebral contact surface of the second portion; and a translation mechanism for providing relative horizontal movement between the complementary portions.

32. The spinal fusion implant kit of claim 31, wherein the at least two spinal fusion implant devices are of different sizes.

33. The spinal fusion implant kit of claim 31, wherein the first and second complementary portions of the first implant device have a different slope than the slope of the first and second complementary portions of the second implant device.

34. The spinal fusion implant kit of claim 31, wherein the kit includes at least one device with a rectangular cross section and at least one device with a rounded cross section.

35. The spinal fusion implant kit of claim 31, wherein the first and second components of a device having a certain size, shape, and slope are interchangeable with the first and second components of other devices having different sizes, shapes, and slopes.

36. A method of surgically adjusting intervertebral spacing, comprising:

gaining exposure to a surgical site;

locating an intervertebral space;

choosing implant components of appropriate size and shape;

locating the components within the intervertebral space; and adjusting the size and shape of the intervertebral space by providing relative horizontal and vertical movement between vertebral contact surfaces of the implant components until a desired positioning is achieved.

* * * * *